(12) United States Patent
Nalagatla et al.

(10) Patent No.: US 8,007,513 B2
(45) Date of Patent: Aug. 30, 2011

(54) PARTIALLY REUSABLE SURGICAL STAPLER

(75) Inventors: Anil K. Nalagatla, Mason, OH (US);
Sudhir B. Patel, Mason, OH (US);
Debasish Pradhan, Sambalpur (IN);
Chester O. Baxter, III, Loveland, OH (US); James Bedi, Cincinnati, OH (US)

(73) Assignee: Ethicon Endo-Surgery, Inc., Cincinnai, OH (US)

( * ) Notice: Subject to any disclaimer, the term of this patent is extended or adjusted under 35 U.S.C. 154(b) by 62 days.

(21) Appl. No.: 12/137,576

(22) Filed: Jun. 12, 2008

(65) Prior Publication Data
US 2009/0308909 A1 Dec. 17, 2009

(51) Int. Cl.
*A61B 17/03* (2006.01)
(52) U.S. Cl. .................. 606/219; 227/175.1; 227/176.1
(58) Field of Classification Search .... 227/175.1–182.1; 606/139, 142, 143, 215, 219
See application file for complete search history.

(56) References Cited

U.S. PATENT DOCUMENTS

| | | | |
|---|---|---|---|
| 4,520,817 A * | 6/1985 | Green | 227/176.1 |
| 4,633,861 A | 1/1987 | Chow et al. | |
| 4,633,874 A | 1/1987 | Chow et al. | |
| 4,892,244 A | 1/1990 | Fox et al. | |
| 5,111,987 A | 5/1992 | Moeinzadeh et al. | |
| 5,129,570 A | 7/1992 | Schulze et al. | |
| 5,188,274 A | 2/1993 | Moeinzadeh et al. | |
| 5,399,133 A | 3/1995 | Haber et al. | |
| 5,415,335 A | 5/1995 | Knodell, Jr. | |
| 5,636,779 A | 6/1997 | Palmer | |
| 5,651,491 A | 7/1997 | Heaton et al. | |
| 5,653,373 A | 8/1997 | Green et al. | |
| 5,941,442 A | 8/1999 | Geiste et al. | |
| 5,988,479 A | 11/1999 | Palmer | |
| 6,131,789 A | 10/2000 | Schulze et al. | |
| 6,817,509 B2 | 11/2004 | Geiste et al. | |
| 7,055,730 B2 | 6/2006 | Ehrenfels et al. | |
| 7,140,527 B2 * | 11/2006 | Ehrenfels et al. | 227/175.1 |
| 7,159,750 B2 * | 1/2007 | Racenet et al. | 227/180.1 |
| 7,169,158 B2 * | 1/2007 | Sniffin et al. | 606/151 |
| 7,172,104 B2 * | 2/2007 | Scirica et al. | 227/175.2 |
| 7,225,963 B2 * | 6/2007 | Scirica | 227/175.2 |
| 7,293,685 B2 * | 11/2007 | Ehrenfels et al. | 227/175.4 |
| 7,334,717 B2 * | 2/2008 | Rethy et al. | 227/175.1 |
| 7,588,176 B2 * | 9/2009 | Timm et al. | 227/179.1 |
| 2004/0094598 A1 | 5/2004 | Geiste et al. | |
| 2004/0108357 A1 | 6/2004 | Milliman et al. | |
| 2005/0267478 A1 * | 12/2005 | Corradi et al. | 606/73 |

(Continued)

OTHER PUBLICATIONS

PCT International Search Report dated Sep. 9, 2009, International Application No. PCT/US2009/047043.

*Primary Examiner* — Paul R Durand
(74) *Attorney, Agent, or Firm* — Dean L. Garner

(57) ABSTRACT

In accordance with the present invention, there is provided a method for performing a surgical stapling procedure by providing a stapler comprising a handle and a staple cartridge with an opposing anvil. The staple cartridge contains a plurality of surgical staples. The stapler also has an actuator module for deploying staples, wherein the actuator has a longitudinally movable member for sequentially ejecting staples towards the anvil. The method involves operating the actuator module so as to eject the plurality of staples, and removing the actuator module from the body and discarding the actuator module. The method also involves sterilizing the body.

1 Claim, 16 Drawing Sheets

U.S. PATENT DOCUMENTS

| | | | |
|---|---|---|---|
| 2006/0144898 A1* | 7/2006 | Bilotti et al. | 227/180.1 |
| 2007/0108252 A1* | 5/2007 | Racenet et al. | 227/176.1 |
| 2007/0194080 A1* | 8/2007 | Swayze et al. | 227/176.1 |
| 2007/0219563 A1* | 9/2007 | Voegele | 606/108 |
| 2007/0233053 A1* | 10/2007 | Shelton et al. | 606/1 |
| 2007/0246508 A1* | 10/2007 | Green | 227/180.1 |
| 2007/0270884 A1* | 11/2007 | Smith et al. | 606/139 |
| 2008/0082115 A1* | 4/2008 | Morgan et al. | 606/153 |

* cited by examiner

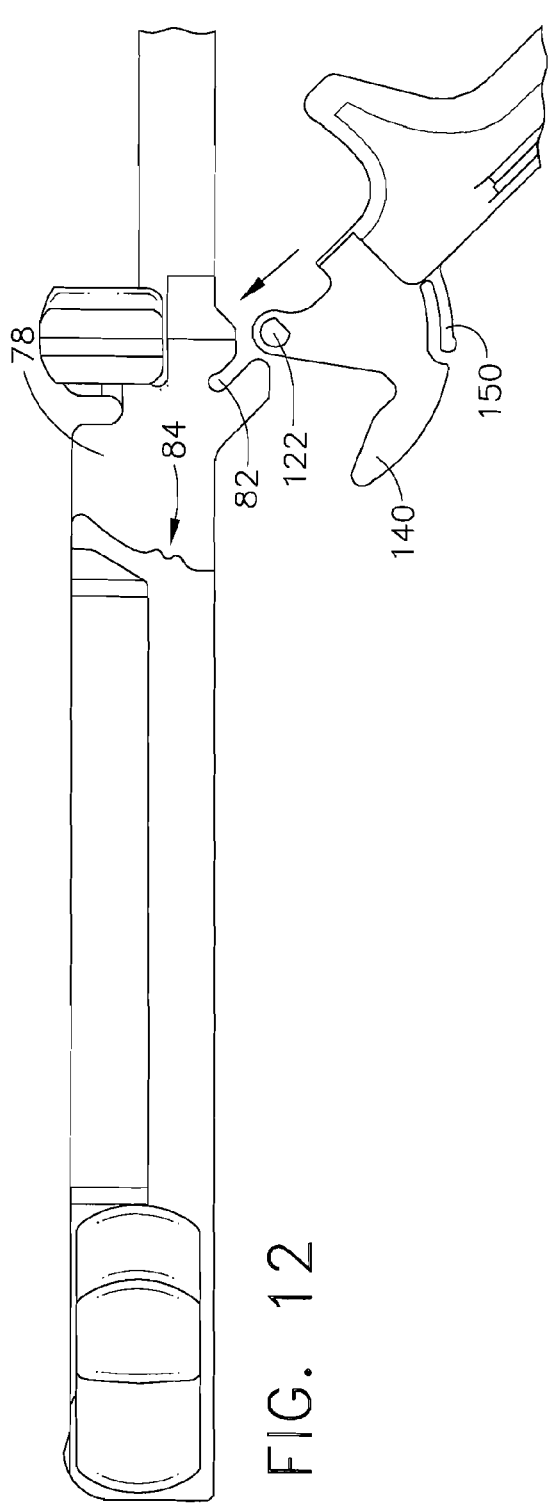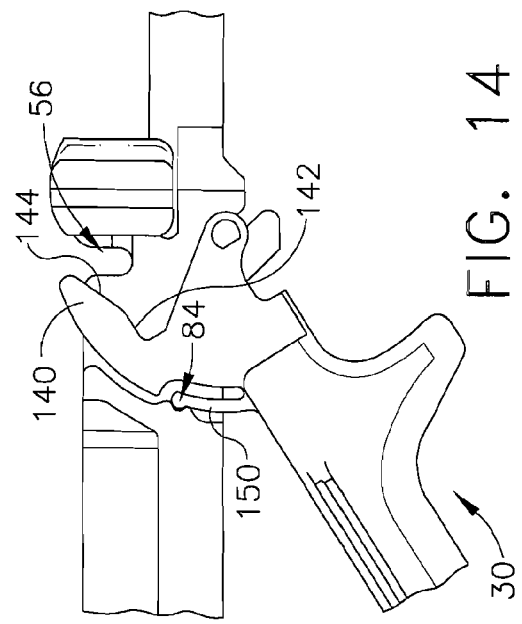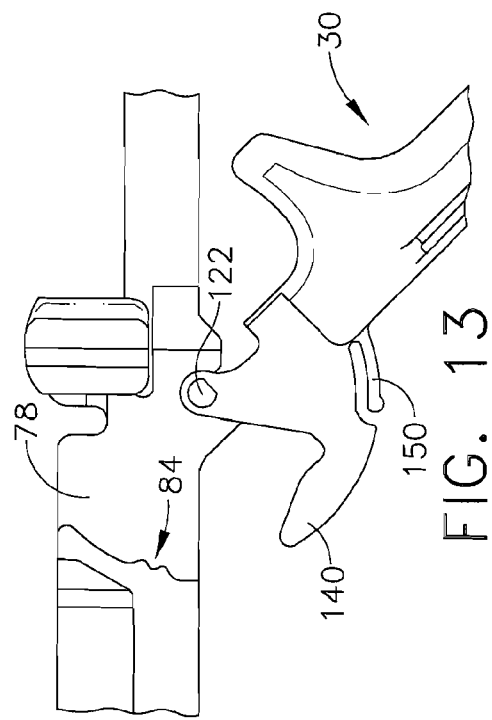

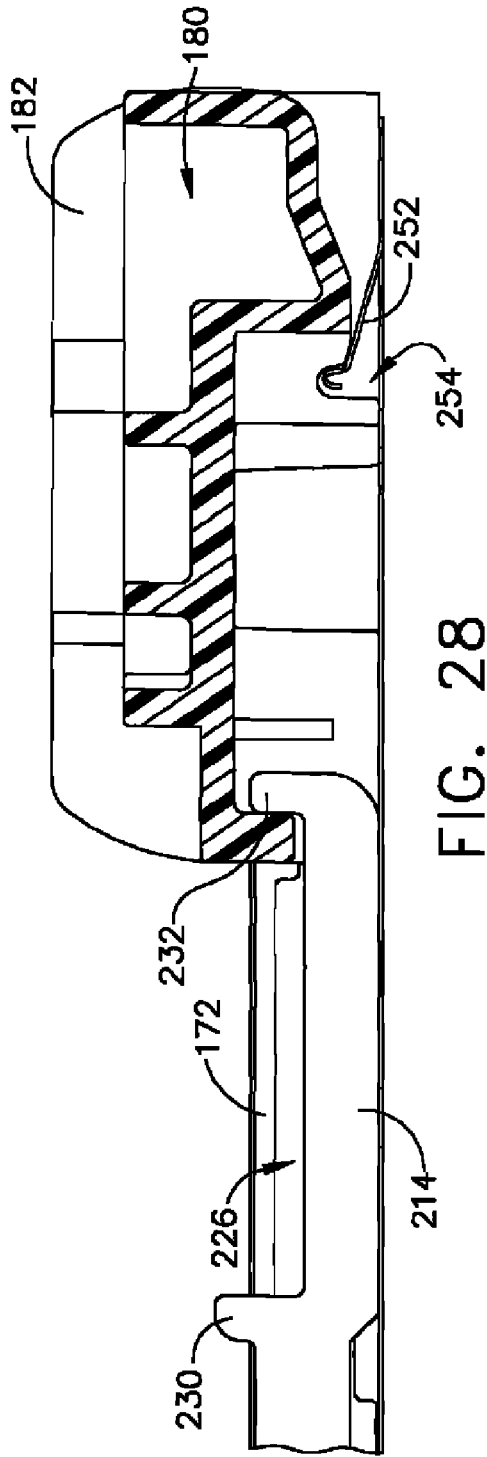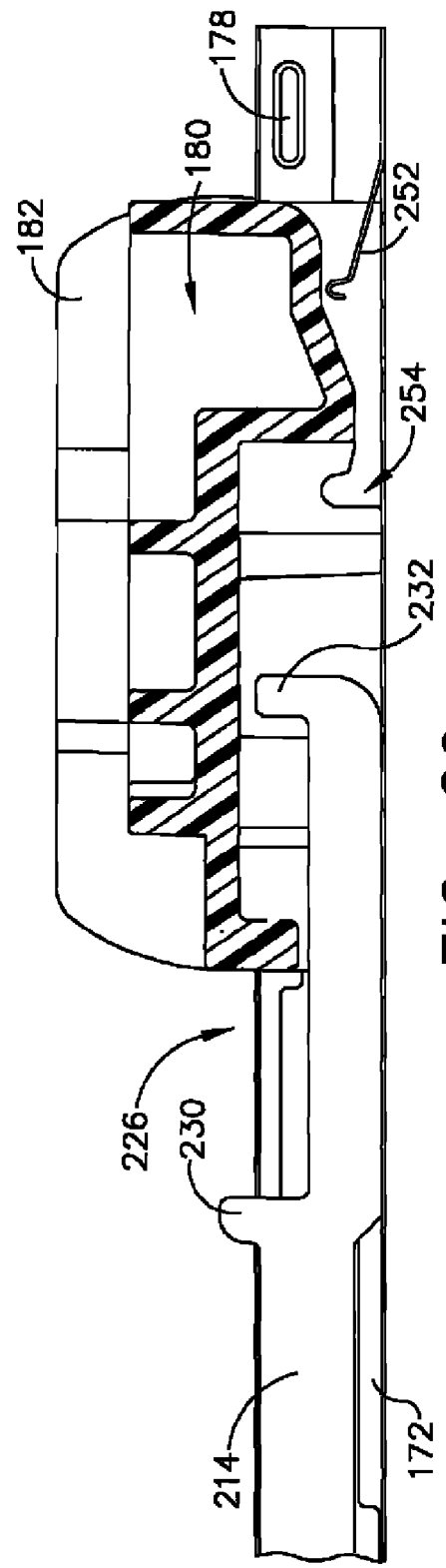

PARTIALLY REUSABLE SURGICAL STAPLER

FIELD OF THE INVENTION

The present invention relates generally to surgical stapling instruments and, more particularly, to a surgical stapler which can be disassembled and portions reconditioned and sterilized for reuse in subsequent surgical procedures, and which includes a removable actuating module that can be reused with multiple staple cartridges during a single patient procedure.

BACKGROUND OF THE INVENTION

Before surgical staplers were introduced, surgeons had to spend a great deal of time sewing the tissue of patients back together. This was the most time intensive aspect of a surgical procedure. Surgical staplers have decreased the amount of time that a user spends sewing tissue back together. Such surgical staplers are described in the following issued U.S. patents which are hereby incorporated herein by reference: U.S. Pat. No. 4,633,861 Chow et al.; U.S. Pat. No. 4,633,874 Chow et al.; and U.S. Pat. No. 5,129,570 Schulze et al.

One concern with surgical staplers has been assuring that the staplers used during a procedure are sterile. Reusable staplers have typically been relatively complicated mechanical instruments which are difficult to sterilize after use. Hence, it was once desired that surgical staplers be completely disposable. As more than one surgical stapler may be required in a surgical procedure, for economical reasons disposable surgical staplers having reloadable staple cartridges have been developed. These reloadable staple cartridges have comprised a combination of staples and a firing module for discharging the staples. Typically the cutting instrument is included in the firing module. Therefore, each time a stapler is reloaded with a new staple cartridge, a new knife and firing assembly is also inserted into the stapler. Numerous staple cartridges are normally used during a single patient procedure, resulting in the repeated replacement of the knife and firing elements for the same patient. Since a knife is usually not worn out after a staple cartridge has been emptied, the knife and firing assembly could be reused with additional staple cartridges within the same patient. Reusing the firing assembly within a single patient procedure would not require additional sterilizing and can decrease the costs incurred during the procedure. Recently, there has also been a desire to make portions of a surgical stapler reusable, so that a portion is disposable and a portion is reusable in subsequent procedures. Reusing portions of the stapler reduces the costs associated with surgical procedures, and also decreases the surgical waste.

Thus, to reduce the costs associated with surgical procedures, there is a need for a surgical stapler that can be disassembled and portions of the stapler reconditioned for subsequent use. In particular, there is a need for a surgical stapler in which the firing and cutting components may be reused with multiple staple cartridges within a single patient procedure in order to decrease the amount of materials utilized with the stapler. There is also a need for a surgical stapler that can be easily assembled and disassembled to allow reconditioning and reuse of some of the stapler parts. In addition, there is a need for a partially reusable stapler that incorporates a disposable firing module to allow the more complex cutting and stapling components to be easily replaced between surgical procedures. Further, there is a need for a partially reusable stapler in which the reusable parts have a simple, one-piece design to facilitate effective reconditioning of the parts between procedures. The present invention provides a partially reusable surgical stapler which achieves these objectives.

SUMMARY OF THE INVENTION

In accordance with the present invention, a partially reusable surgical stapler is provided for deploying staples into tissue. The stapler has a body with a distal end, a proximal end and a longitudinal axis therebetween. The proximal end includes a handle while the distal end includes a staple cartridge holder and an opposing anvil. The stapler also has an actuator module for deploying staples. The actuator module includes at least one longitudinally movable member for sequentially ejecting staples towards the anvil. The actuator module is readily removable and replaceable to and from the body.

In another embodiment, the present invention provides a partially reusable surgical stapler having an upper jaw member with a proximal handle end and a distal anvil end. A lower jaw member having a proximal channel-shaped frame and a distal staple cartridge channel is aligned with the upper jaw. An actuator module, having at least one longitudinally moveable member for sequentially ejecting staples towards the anvil, is readily removable and replaceable to and from the lower jaw frame. A staple cartridge containing a plurality of staples is removably disposed within the staple cartridge channel. A latching member for connecting the upper and lower jaws together is provided at an intermediate position along a longitudinal axis of the stapler. The latching member is moveable relative to the upper and lower jaw members to place the stapler in a series of different locking states. The different locking states include an assembly state for connecting and disconnecting the latching member to the jaw members, and a closed, latched state in which the latching member is locked to the jaw members.

BRIEF DESCRIPTION OF THE DRAWINGS

FIG. 12 is a partial front view of the stapler showing the latching member in a ready to assemble state;

FIG. 13 is a partial front view of the stapler showing the latching member in an initial inserted state;

FIG. 14 is a partial front view of the stapler showing the latching member in a rotated and partially locked-in state;

FIG. 26 is a close-up, isometric view of the distal end of the actuating module showing the protector cap;

FIG. 28 is a sectional view of the actuating module proximal end, showing the relationship between the actuating knob and the detent spring in a full back position; and FIG. 29 is a sectional view of the actuating module proximal end, showing the actuating knob moved forward during firing.

DETAILED DESCRIPTION OF THE INVENTION

Figure 1:
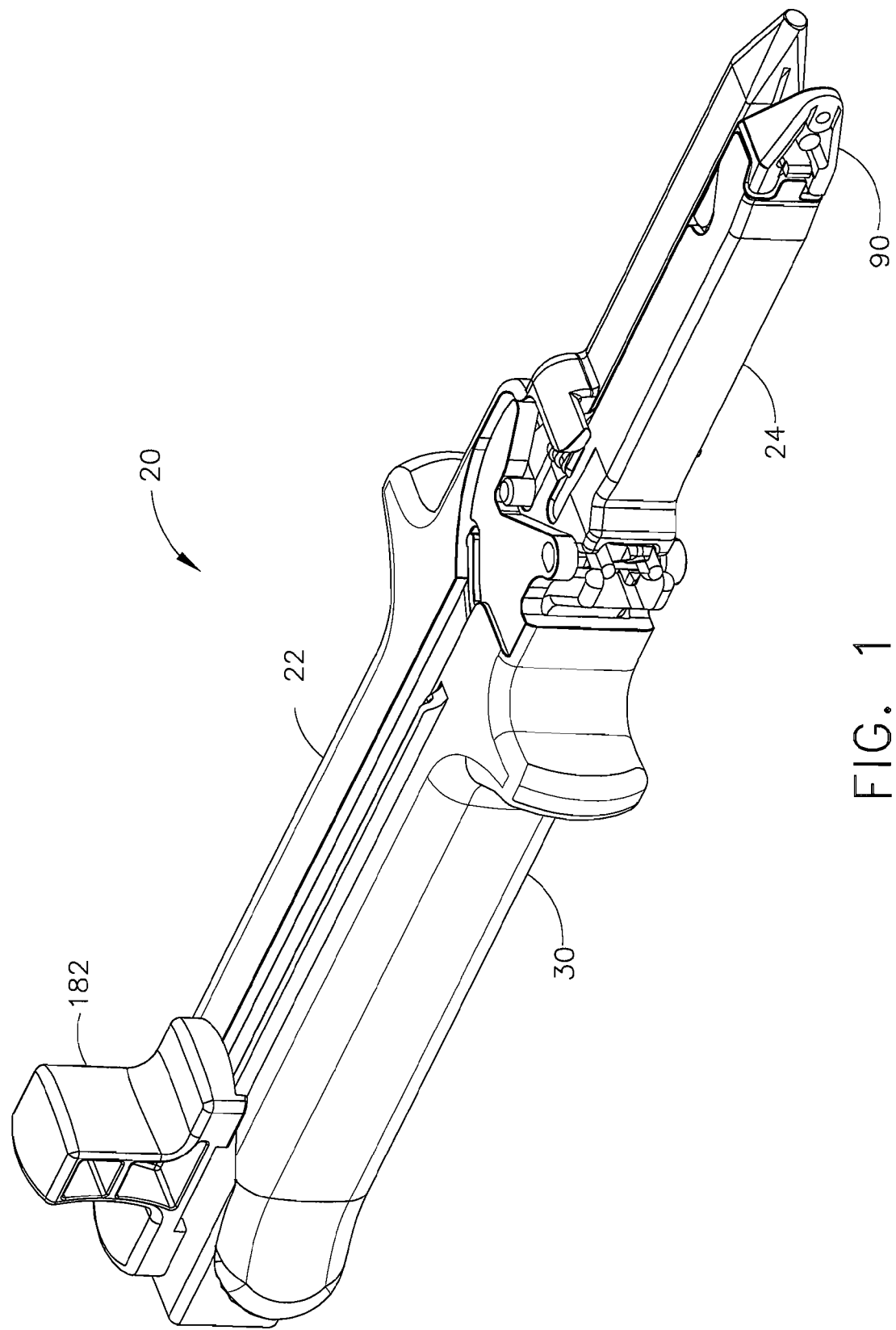
FIG. 1 is an isometric view of an exemplary surgical stapler showing the stapler in a closed position.
Figure 2:
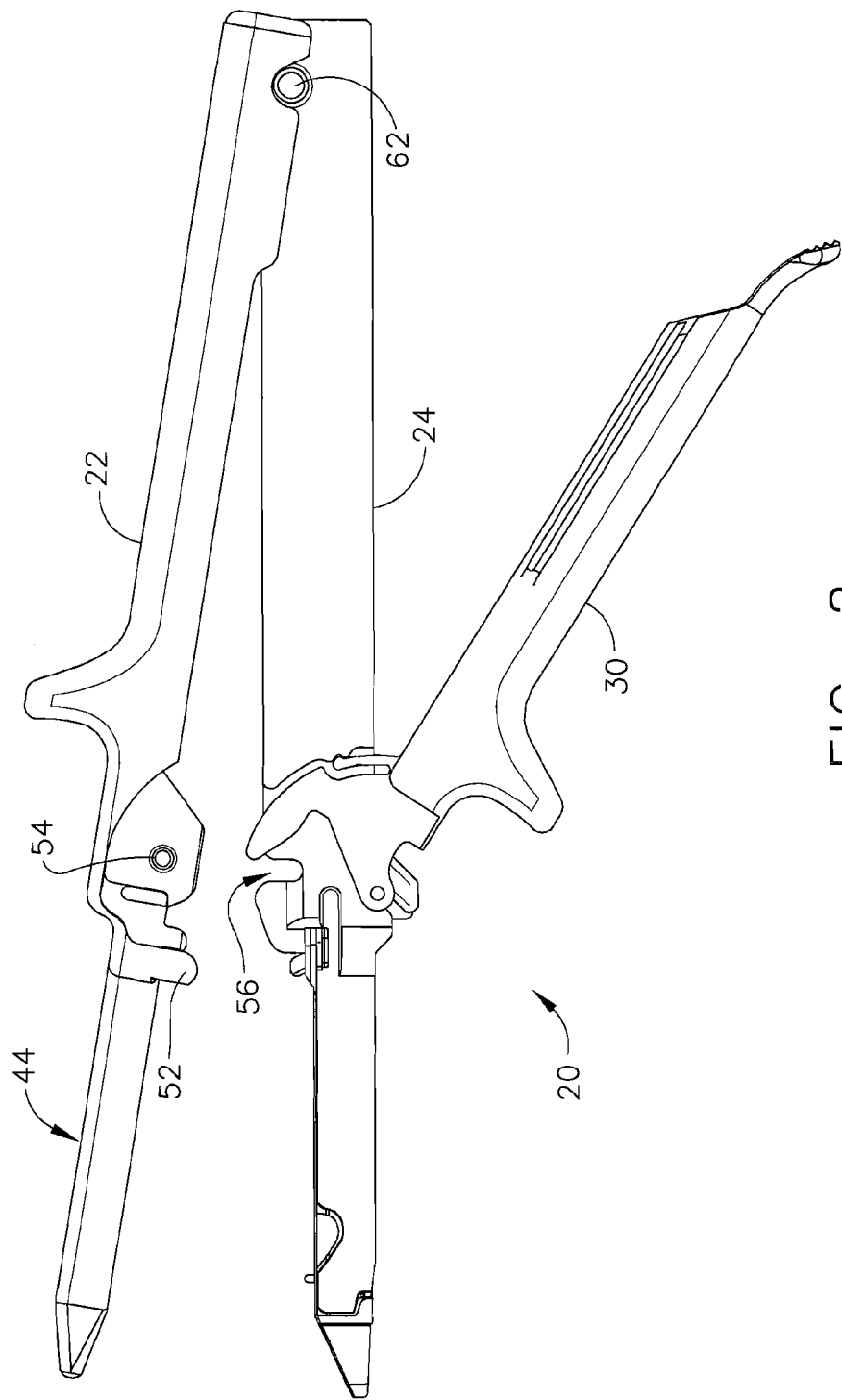
FIG. 2 is a front view of the stapler in an open position.
Figure 3:
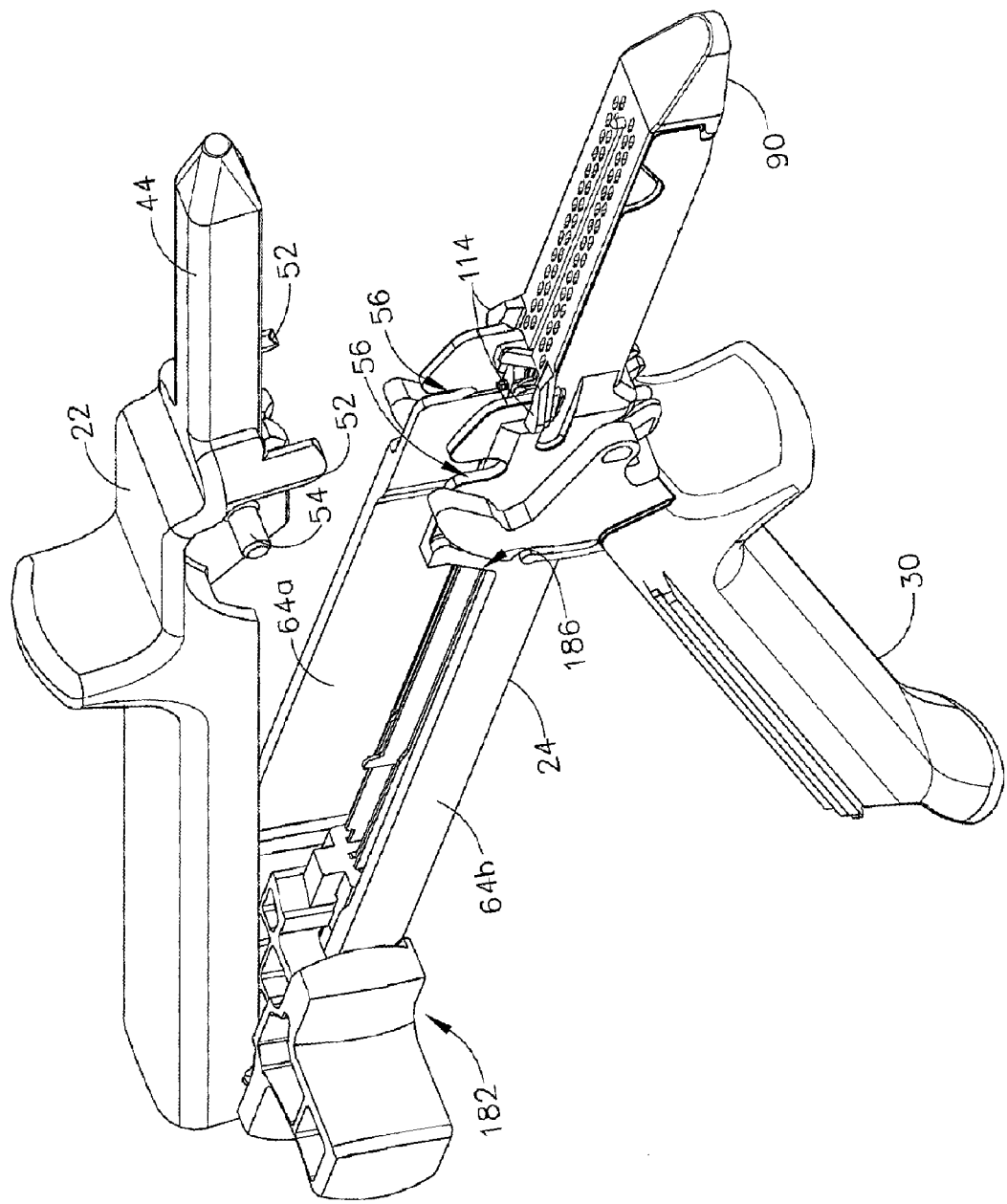
FIG. 3 is an isometric view of the stapler in an open position.

Referring now to the drawing figures, in which like numerals indicate like elements throughout the views, FIGS. 1 through 3 illustrate a first exemplary surgical stapler 20 of the present invention. The body of stapler 20 includes an upper jaw member 22, a lower jaw member 24, and a latching member 30. Latching member 30 is pivotable relative to the upper and lower jaws members 22, 24, as shown in FIGS. 2-3. Latching member 30 can be pivoted through a series of different latching states to lock the stapler closed for use or to open the stapler varying degrees to allow for adjustment of tissue within the stapler, the replacement of a staple cartridge, or disassembly of the stapler. Upon completion of a surgical procedure, latching member 30 can be pivoted to a fully open position to allow stapler 20 to be disassembled in preparation for the resterilization and reuse of portions of the stapler.

Figure 4:
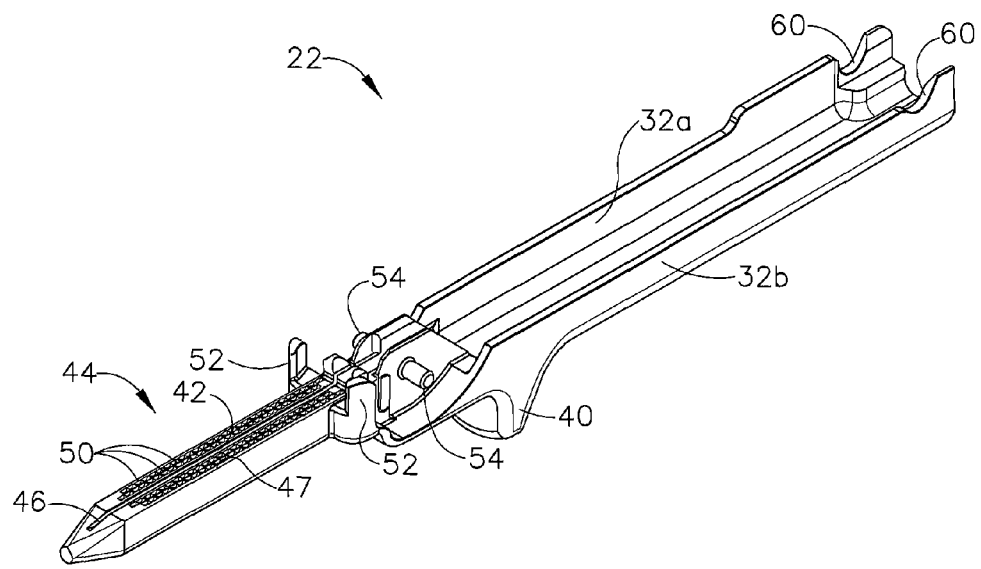
FIG. 4 is an isometric bottom view of the reusable upper jaw member for the stapler.
Figure 5:
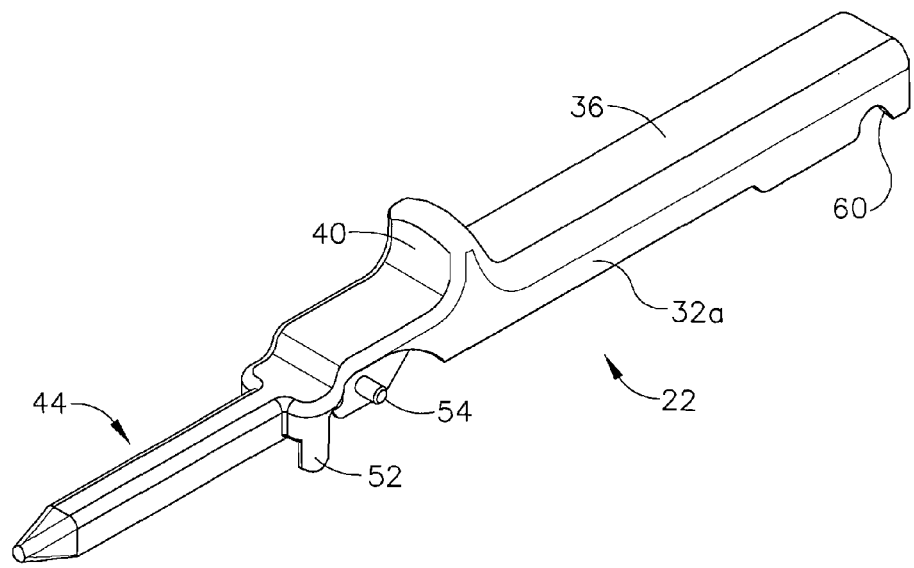
FIG. 5 is an isometric top view of the stapler upper jaw member.

As shown in FIGS. 4 and 5, upper jaw 22 comprises a single piece, elongated channel-shaped frame having a pair of opposing sidewalls 32a, 32b connected by a top wall 36. Top wall 36 is suitably shaped on the outer surface to form a hand grip and includes an upper handle protrusion 40 to facilitate the handling and operation of the stapler by a surgeon. The distal end of upper jaw 22 comprises a pair of inwardly extending flanges 42 which define an anvil 44 of the stapler. Flanges 42 are separated by a central, longitudinal slot 46 which extends along the entire length of anvil 44. The inner surface of each flange 42 is provided with two longitudinal rows of uniformly spaced staple-forming pockets 50. Staple forming pockets 50 allow the fashioning of B-form staples when U-shaped staples are ejected against the anvil flanges during firing. Anvil 44 includes a tapered tip at the distal-most end for facilitating insertion of the stapler into hollow, tubular body organs. A pair of tissue stops 52 is provided on opposite sides of anvil 44 adjacent the proximal end of staple forming pockets 50. Tissue stops 52 are laterally aligned with the proximal end of staple forming pockets 50 to prevent tissue from being placed into the stapler beyond anvil 44. Blocking tissue at the proximal end of anvil 44 prevents the pinching or cutting of unstapled tissue.

Cylindrical pins 54 extend from opposite sides of upper jaw 22 proximal of tissue stops 52. Pins 54 fit inside vertical slots on lower jaw 24 to connect the upper and lower jaws together. Upper jaw 22 also includes a pair of curved notches 60 near the proximal end of channel sidewalls 32a, 32b. Notches 60 interact with projections 62 on lower jaw 24, as shown in FIG. 2, to provide a means for easily aligning the jaws during use. Upper jaw 22 is preferably comprised of a single piece of a biocompatible metal, such as, for example, stainless steel. Using a single piece of material for upper jaw 22 increases the structural integrity of the stapler. Alternatively, upper jaw 22 can be manufactured as two or more separate pieces that are joined together during the manufacturing process by known joining methods such as, for example, welding.

Figure 6:
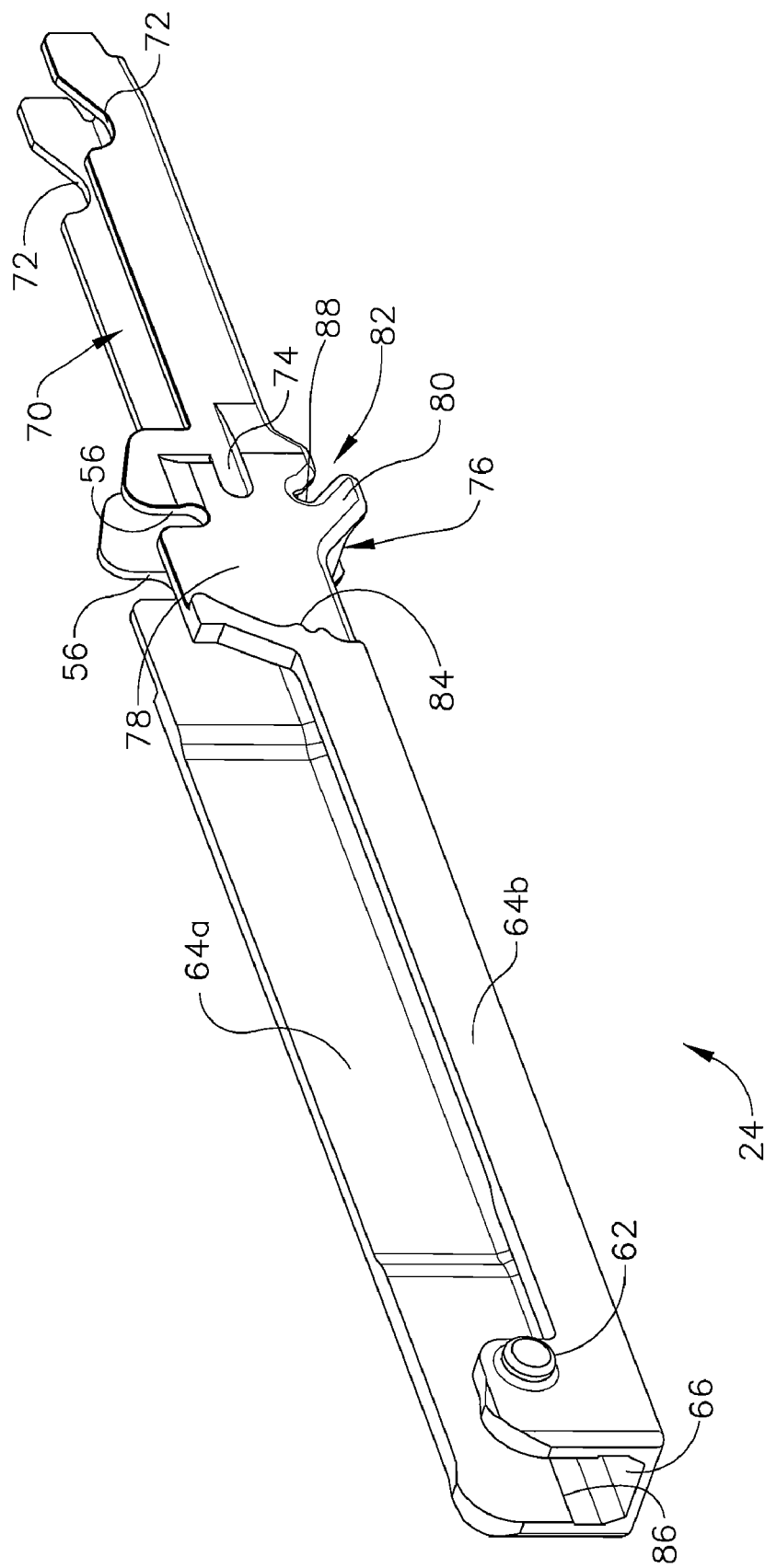
FIG. 6 is an isometric view of the reusable lower jaw member including the cartridge channel.

As shown in FIG. 6, lower jaw 24 comprises a single piece, elongated U-shaped frame having a pair of sidewalls 64a, 64b connected by a bottom wall 66. At the distal end of lower jaw 24, side walls 64a, 64b are reduced in size to form a cartridge channel 70 for supporting a single use staple cartridge within the stapler. Notches 72 are provided in sidewalls 64a, 64b adjacent the distal end of cartridge channel 70. Notches 72 engage side projections on the staple cartridge to hold the cartridge within the channel. Vertical alignment slots 56 are located proximal of cartridge channel 70 in the upper edge of sidewalls 64a, 64b. As mentioned above, pins 54 on upper jaw 22 interface with alignment slots 56 to align and connect the jaw members together. The width between upper jaw sidewalls 32a, 32b is slightly greater than the width between lower jaw sidewalls 64a, 64b to enable the upper jaw to fit over the lower jaw when pins 54 are inserted into alignment slots 56, and projections 62 into notches 60. Indentations 74 are formed in the outer surface of sidewalls 64a, 64b, distal of alignment slots 56. Indentations 74 facilitate the attachment of an actuating module to lower jaw member 24, as will be described in further detail below.

An opening 76 is formed through bottom wall 66 at an intermediate position along lower jaw 24. Sidewalls 64a, 64b extend downward on opposite sides of opening 76 to form distally angled projections 80. Along the distal edge of projections 80, sidewalls 64a, 64b are shaped to form a straight-sided slot 82 having a circular end 88. The diameter of circular end 88 is slightly larger than the width of the slot 82. Proximal of projections 80 the outer surfaces of sidewalls 64a, 64b include a latching member positioning feature. As shown in FIG. 6, the positioning feature can comprise a plurality of detent bumps 84, or other surface indentations, that are machined into the surface of the sidewalls 64a, 64b. FIG. 6 shows only a positioning feature on the front side of lower jaw 24, however, it should be understood that the back side of the lower jaw is fashioned in the same manner so that latching member 30 may be retained in a series of latching states by both sides of the lower jaw, as will be described below. A retention feature 86 is formed at the proximal end of lower jaw 24 at the junction between sidewalls 64a, 64b and bottom wall 66. Retention feature 86 can comprise an inward expansion of sidewalls 64a, 64b which facilitates a snap connection with an actuating module during assembly of stapler 20.

Figure 7:
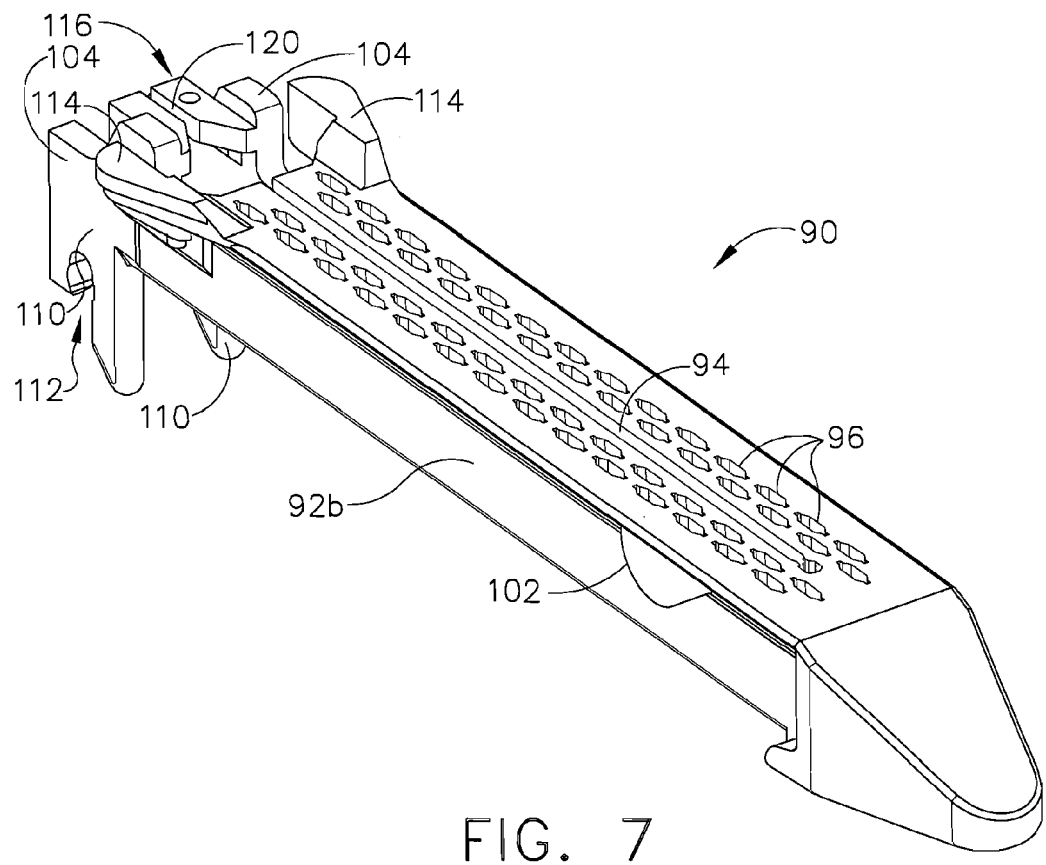
FIG. 7 is an isometric view of the disposable staple cartridge.
Figure 8:
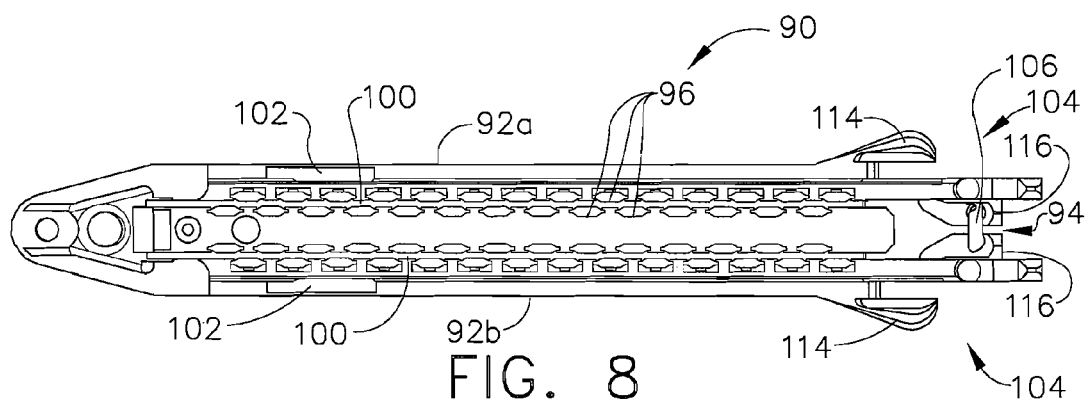
FIG. 8 is a bottom view of the disposable staple cartridge.

FIGS. 7 and 8 show an exemplary removable staple cartridge 90 for use in stapler 20 of the invention. Cartridge 90 is adapted to receive a plurality of surgical staples arranged in at least two laterally spaced longitudinal rows. Cartridge 90 has a body which includes opposite side walls 92a, 92b configured to be slidably received in the interior of lower jaw cartridge channel 70. Staple cartridge 90 is divided longitudinally by a central elongated slot 94 which extends from the proximal end of the cartridge toward its distal end. A plurality of staple openings 96, defined by the cartridge body, are disposed along the elongated center slot 94. In the illustrated embodiment, the staple openings are arranged in two laterally spaced, staggered rows, with each pair of rows disposed on opposite sides of central longitudinal slot 94. The staple openings in adjacent rows are staggered to provide more effective stapling of the tissue when the instrument is operated. Referring to FIG. 8, staple cartridge 90 includes a pair of longitudinal slots 100 located on opposite sides of elongated central slot 94 and disposed between the staggered rows of openings 96. Each longitudinal slot 100 extends from the proximal end of cartridge 90 towards the distal end. A plurality of staple drivers (not shown) are slidably mounted in staple openings 96 for actuating the staples which are loaded into staple cartridge 90. Each staple driver is designed to simultaneously actuate two staples located in the adjacent rows provided in staple cartridge 90. Thus, a first set of staple drivers is provided for actuating the staples in the staggered rows located on one side of central longitudinal slot 94, and a second set of staple drivers is provided for actuating the staples in the pair of adjacent rows located on the other side of the central longitudinal slot.

The distal end of staple cartridge 90 includes a tapered tip to facilitate the insertion of lower jaw member 24 into a hollow tubular body organ. Proximal of the tapered tip, staple cartridge 90 is provided with a pair of outwardly extending protrusions 102. A pair of spaced, parallel flanges 104 extends rearward from opposite sides of staple cartridge 90. Legs 110 extend downward from flanges 104 at the proximal end of the staple cartridge. Each leg 110 is provided with a rounded, downwardly facing notch 112. When cartridge 90 is assembled on lower jaw 24, protrusions 102 are loosely received in notches 72 in the lower jaw side walls, and legs 110 extend through opening 76 in the lower jaw bottom wall 66. Leg notches 112 engage a pin on latching member 30, as will be described below, to hold the cartridge within lower jaw channel 70. A pair of wings 114 extends upward and outward from sidewalls 92a, 92b at the proximal end of cartridge 90. Wings 114 function as finger grips which allow staple cartridge 90 to be manually inserted into and removed from lower jaw 24. Using wings 114, cartridge 90 can be lifted out of jaw opening 76 and notches 72, to remove the cartridge from lower jaw 24 following use. Additionally, wings 114 engage lower jaw sidewalls 64a, 64b at the proximal end of cartridge channel 70, as shown in FIG. 3, to lock the cartridge in place within lower jaw 24. A short extension 116 is formed at the rear of cartridge 90 and located between rearwardly projecting legs 110. Central knife slot 94 extends longitudinally through extension 116, which can be provided with inwardly sloped guide surfaces on its opposite sides at the proximal end of the slot. A lock out pin 106 is connected at one end to extension 116 and is pivotable about the connection point. Initially, when staple cartridge 90 is loaded into stapler 20, lock out pin 106 extends transversely across central knife slot 94.

As mentioned above, stapler 20 includes a latching member 30 for connecting the upper and lower jaws members together at an intermediate position along the longitudinal length of the stapler. Preferably, jaw members 22, 24 are connected together at a location adjacent to the proximal ends of anvil 44 and staple cartridge 90. In the preferred embodiment, shown in FIG. 9, latching member 30 comprises a single piece, channeled-shaped frame having opposing side walls 124a, 124b connected by a top wall 130. Latching member 30 further includes a latch pin 122 for pivotally connecting the latching member to lower jaw 24. Preferably, the latching member is comprised of a single piece of stainless steel, or another similar biocompatible metal. The distance between the opposing latching member side walls 124a, 124b is sufficient to span the sidewalls 64a, 64b of lower jaw 24. Side walls 124a, 124b include outwardly extending, elongated flanges 132 which serve as finger grips to enable latching arm 120 to be manually pivoted between latching positions. The outer surface of latching arm 120 includes a handle extension 134. When connected to lower jaw member 24, handle extension 134 combines with upper jaw handle extension 40 to form a hand grip for manipulation of the stapler by a surgeon.

Figure 9:
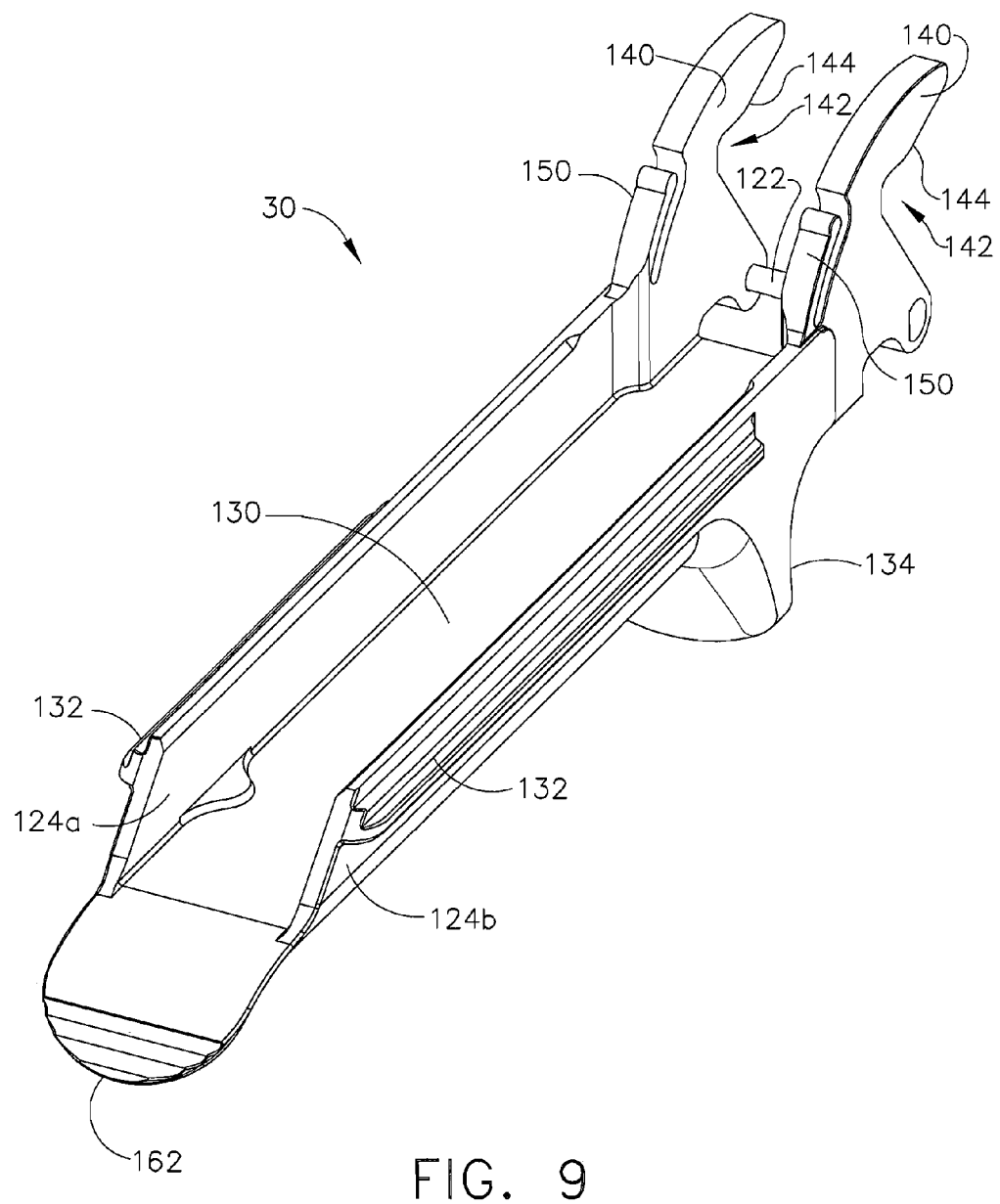
FIG. 9 is an isometric view of the reusable latching member.
Figure 10:
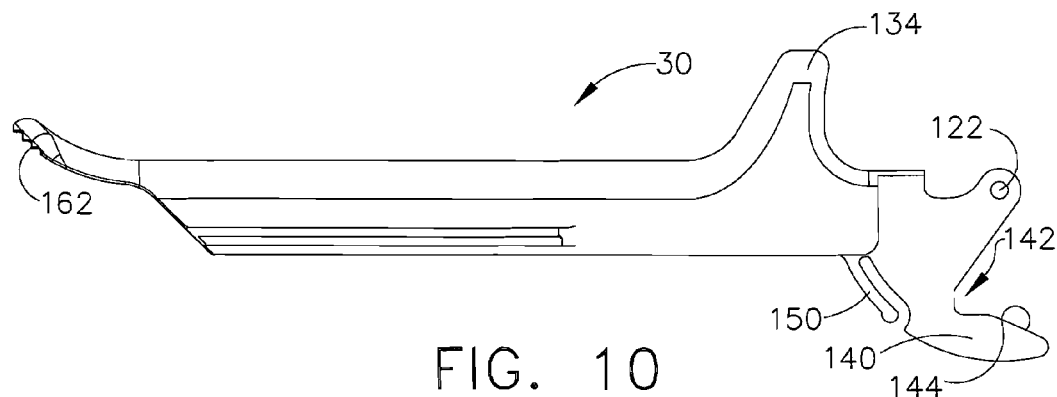
FIG. 10 is a front view of the reusable latching member.
Figure 11:
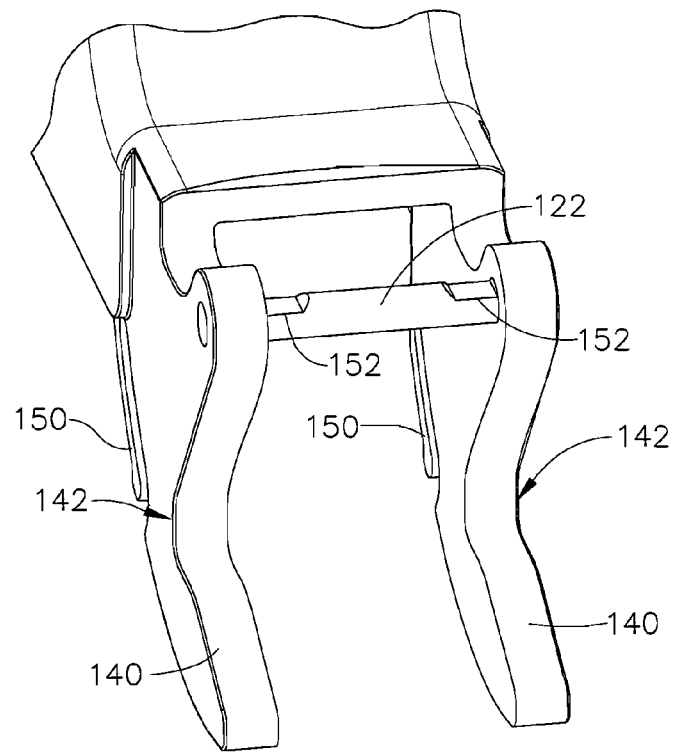
FIG. 11 is a detailed isometric view of the distal end of the latching member.

Each side wall 124a, 124b of latching member 30 includes a distally-extending C-shaped hook member 140 provided with a forwardly facing notch 142 for engaging upper jaw pins 54. As shown in FIGS. 9 and 10, hook members 140 include an inner cam surface 144 extending rearward from the tip of the hook member into notch 142. When latching member 30 is moved to a closed, operative state, notches 142 engage upper jaw pins 54, acting as an over-center latch to maintain the latching member in the latched state. Below notches 142, each hook member 140 projects distally downward, beyond the end of latching member top wall 130. Latch pin 122 extends between the down turned ends of hook members 140, as shown in FIG. 11, across the end of latching member 30. Latch pin 122 has a cylindrical shape with flat surfaces 152 adjacent each end. The diameter of latch pin 122 is greater than the narrow opening for lower jaw slot 82. Latching member 30 is detachably connected to lower jaw 24 by inserting latch pin 122 into lower jaw slot 82. Latch pin 122 is inserted into slot 82 by orienting latching member 30 so that flat ends 152 lie in parallel with the straight sides of the slot. In this position, latch pin 122 can be inserted into slot 82 despite the pin diameter being greater than the slot width. With flat ends 152 aligned with the linear sides of slot 82, latch pin 122 is inserted into the slot, as shown in FIG. 12, until the pin rests within circular slot end 88, as shown in FIG. 13.

Stapler 20 also includes means for retaining the latching member in a series of different latching states. Referring to FIGS. 9 and 10, the retaining means includes a spring arm 150 extending from the top edge of each latching arm sidewall 124a, 124b. Spring arm 150 curves distally upward, following the upper contour of hook member 140, and includes a bulbous free end. With latching pin 122 assembled within slot 82, and latching member 30 angled distally, as shown in FIG. 13, stapler 20 is in an initial, open state. To close stapler 20, latching member 30 is rotated towards the proximal end of the stapler, to draw the latching member closer to the body of lower jaw member 24. As flat ends 152 rotate out of alignment with the sides of slot 82, the difference in width between pin 122 and slot 82 prevents the pin from slipping out of slot end 88. Pin 122 is thus fixed within slot end 88, locking latching member 30 to lower jaw member 24.

As latching member 30 rotates, hook members 140 are drawn along the sides of lower jaw member 24. As hook members 140 swing alongside lower jaw sidewalls 64a, 64b, the bulbous ends of spring arms 150 contact detent bumps 84 on the sidewalls. To move spring arms 150 between the detent bumps 84, additional force is applied to latching member 30 to cause the spring arms to flex towards the hook members 140, so that the ends of the spring arms can ride over the bumps. With spring arms 150 positioned between detent bumps 84, as shown in FIG. 14, latching member 30 is in a partially locked-in state. In the partially locked-in state, latching member 30 is attached to lower jaw 24 and alignment slots 56 are just distal of the tip of hook members 140. Upper jaw pins 54 can be freely inserted or removed from lower jaw slots 56, allowing the upper and lower jaw members to be separated and rejoined together.

Figure 15:
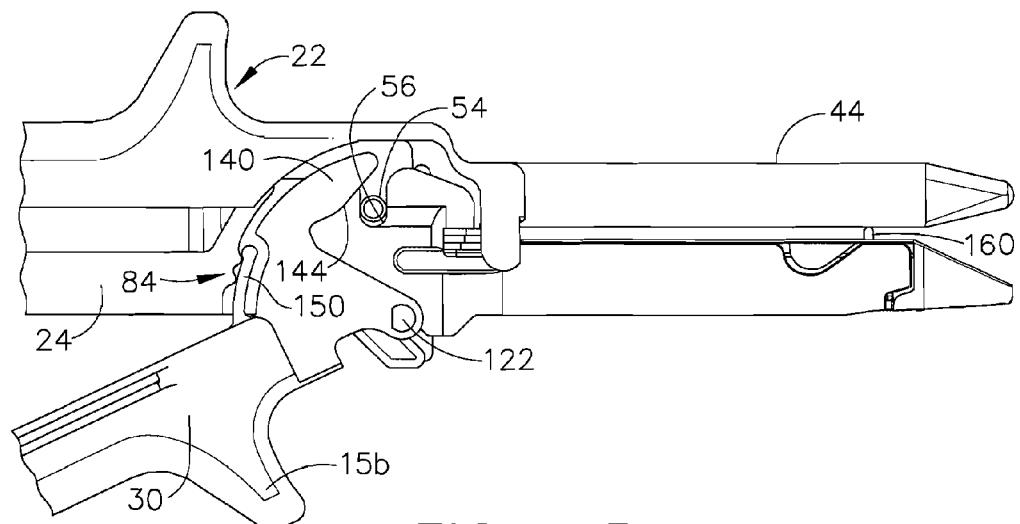
FIG. 15 is a partial front view of the stapler showing the relative positions of the latching and upper jaw members in a pre-close position.

As latch pin 122 continues to rotate within slot end 88, drawing latching member 30 closer to lower jaw member 24, hook member inner cam surfaces 144 rotate over the opening of alignment slots 56, blocking the slots and locking upper jaw pins 54 within the slots. Spring arms 150 also ride along detent bumps 84 to engage the concave outer edge of the top bump. In this pre-closed state, shown in FIG. 15, latching member 30 and upper and lower jaw members 22, 24 are connected together to form the body of stapler 20, but upper jaw pins 54 can slide within slots 56, between the bottom of the slot and cam surface 144, to allow some relative movement between the jaw members. Latching member 30 maintains the jaw members in a loosely latched position to permit relative movement between the staple cartridge and anvil. The relative movement at the distal end of jaw members 22, 24 allows for tissue adjustments without disconnecting the jaw members from each other.

Figure 16:
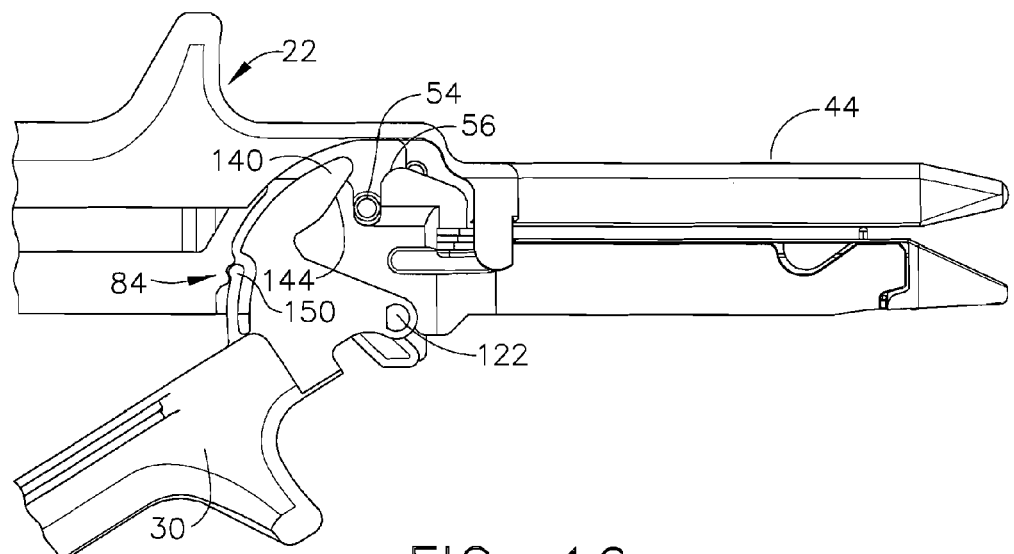
FIG. 16 is a partial front view of the stapler showing the relative positions of the latching and upper jaw members in an open position during use.

When latching member 30 is rotated to a closed, operative state (shown in FIG. 1) the latching member surrounds lower jaw member 24, and pins 54 on upper jaw member 22 are lodged within hook member notches 142. Spring arms 150 advance distally upward along the sides of lower jaw member 24 beyond detent bumps 84. In this state, the upper and lower jaw members are locked together to compress tissue between the anvil and cartridge surfaces, and the stapler is ready for stapling and cutting tissue. In the closed state, a minimum spacing may be maintained between the anvil and cartridge surfaces by a spacer pin 160. To adjust the placement of tissue between the anvil and cartridge surfaces, latching member 30 can be rotated back to the pre-close state, as shown in FIG. 16, to dislodge pins 54 from hook member notches 142. As latching member 30 rotates back, spring arms 150 reengage with detent bumps 84 to hold the latching member in place. Returning to the pre-close state loosens the connection between hook members 140 and pins 52, to allow the pins to slide within slots 56 without disconnecting the upper and lower jaws.

To disassemble stapler 20, latching member 30 is rotated away from lower jaw member 24 to draw upper jaw pins 54 out of hook notches 142. Latching member 30 may be rotated away from upper and lower jaw members 22, 24 by pulling on the curved latching arm tip 162. As a counter rotating force continues on latching arm 120, spring arms 150 move through detent bumps 84, enabling hook members 140 to swing through and way from the lower jaw sidewalls 64a, 64b. Latching member 30 is rotated around in the direction of staple cartridge 90 until latching member 30 returns to the initial, open position shown in FIG. 13. With latching member 30 in the open state, flat ends 152 on latch pin 122 are again aligned in parallel with the straight sides of slot 82, enabling the latch pin to be withdrawn through slot 82 to separate the latching member from lower jaw member 24. With latching member 30 detached, stapler 20 can be disassembled into three separate, one-piece components, namely, upper jaw 22, lower jaw 24 and latching member 30. The one-piece channel-shaped construction of these reusable components provides for easy yet thorough reconditioning and sterilization of the components between uses.

Figure 17:
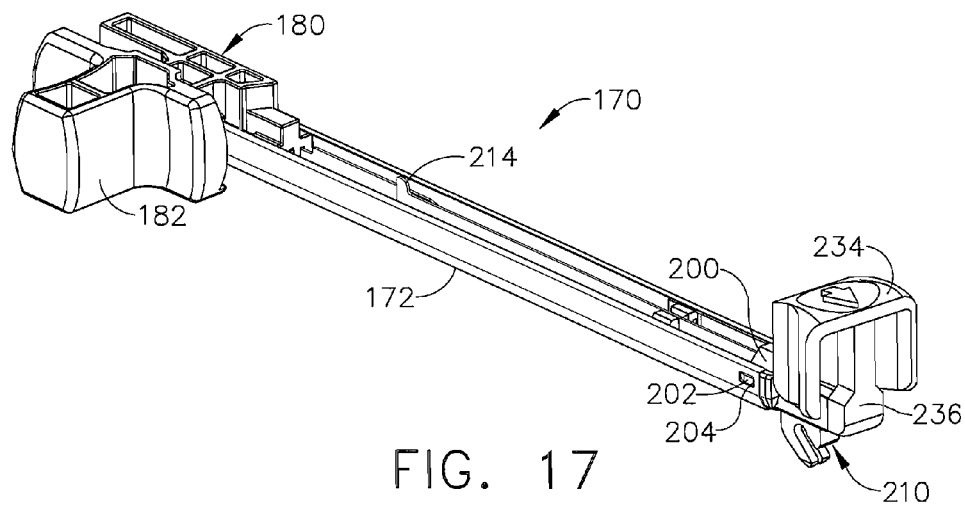
FIG. 17 is an isometric view of the disposable actuating module.
Figure 18:
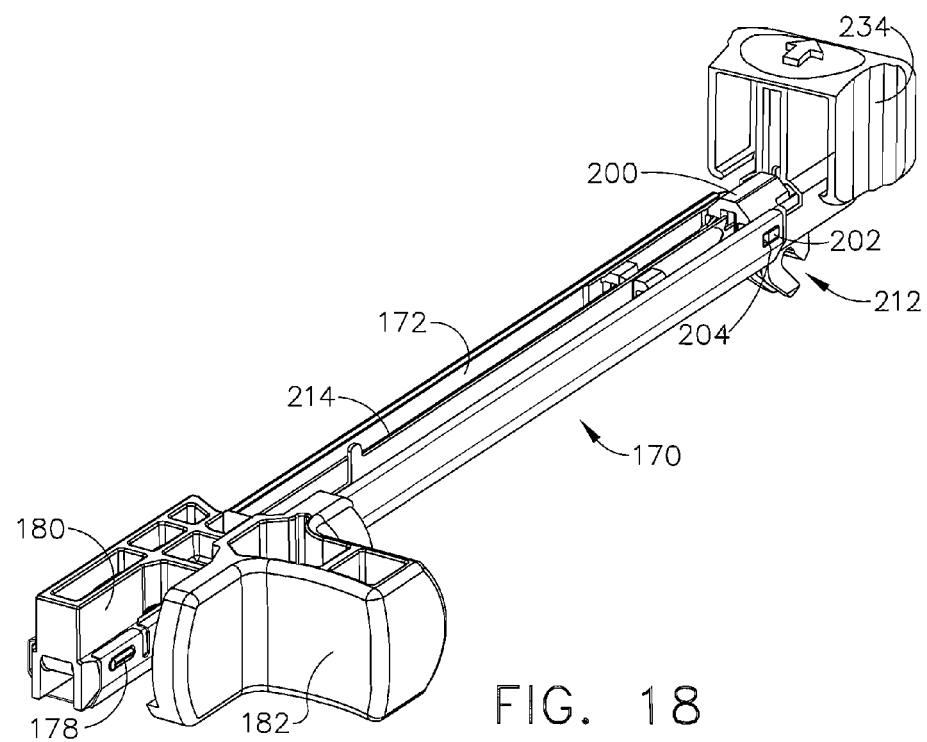
FIG. 18 is another isometric view of the disposable actuating module looking forward from the proximal to the distal end.
Figure 19:
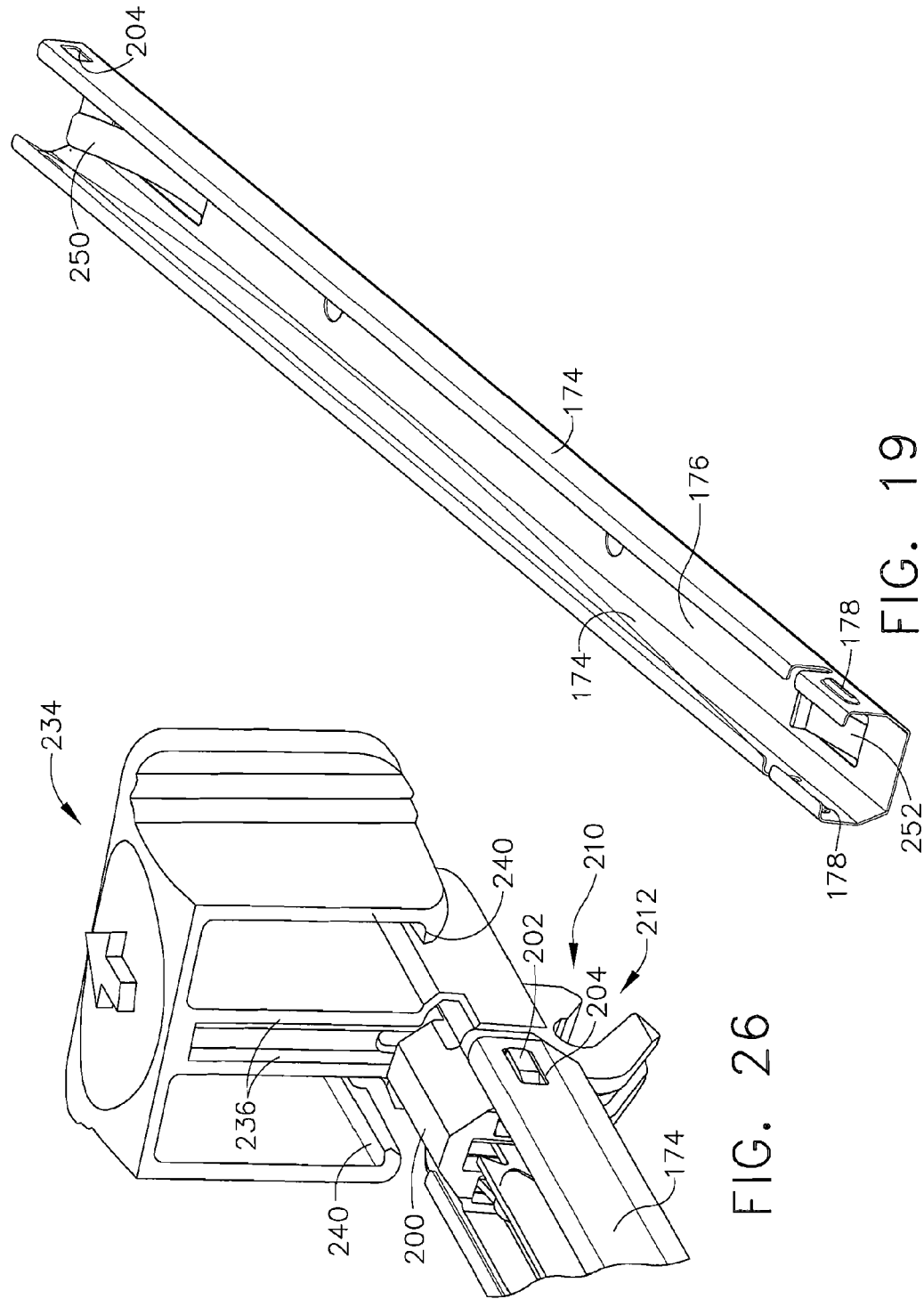
FIG. 19 is an isometric view of the actuating module pan.
Figure 20:
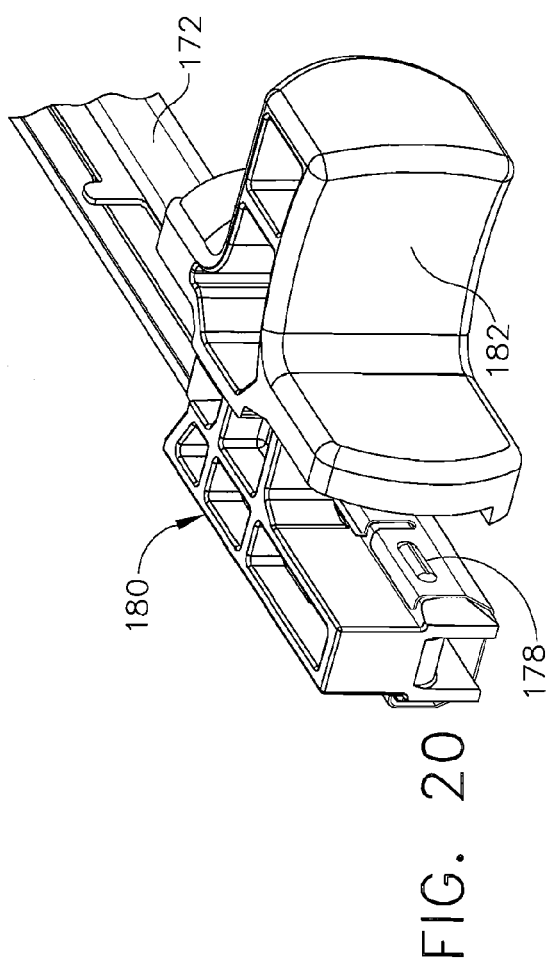
FIG. 20 is a detailed, isometric view of the proximal end of the actuating module.

Turning now to FIGS. 17 and 18, which show an actuator module 170 for stapling and cutting tissue clamped between the upper and lower jaw members 22, 24. Actuator module 170 comprises a U-shaped, longitudinal module pan 172 which provides the supporting structure for the actuator module components. Module pan 172 includes a pair of sidewalls 174 connected together by a bottom wall 176 (FIG. 19). The distance between module pan sidewalls 174 is less than the distance between lower jaw sidewalls 64a, 64b to enable the module pan to be slidably mounted within the proximal channel of lower jaw 24. As shown in FIGS. 19 and 20, the proximal end of module pan 170 includes one or more detent bumps 178 protruding from the outer surface of sidewalls 174. Detent bumps 178 engage retention features 86 on the inside channel of lower jaw member 24 when the actuator module 170 is slid proximally into the lower jaw channel. The interaction of detent bumps 178 with retention features 86 snaps and retains the actuator module in place within lower jaw member 24.

Figure 21:
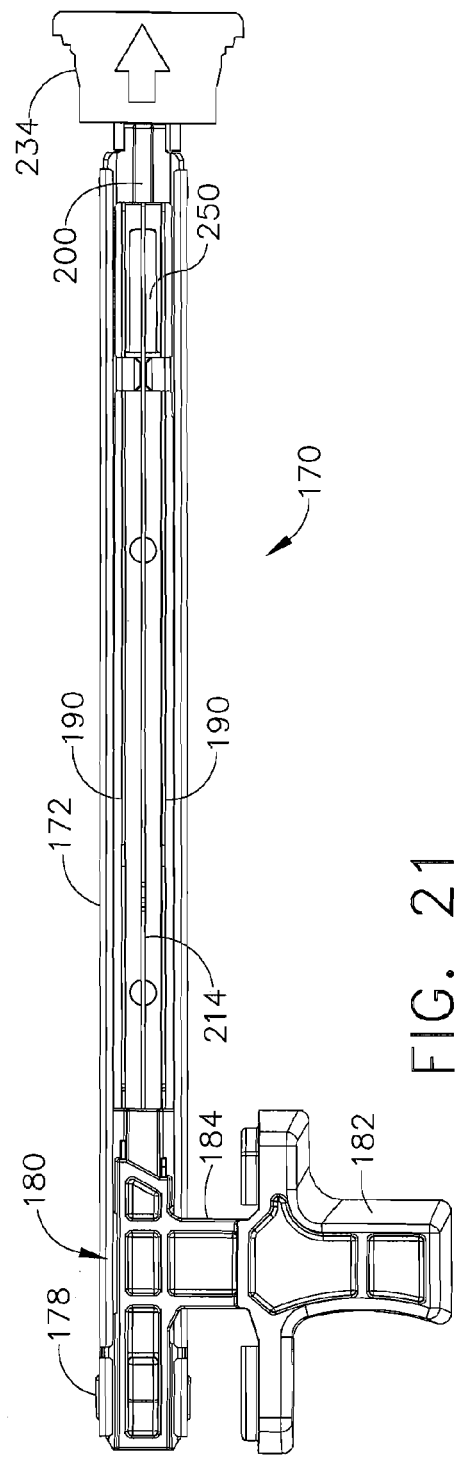
FIG. 21 is a top view of the actuating module.

As shown in FIG. 21, a plurality of moveable actuating members are situated within module pan 172 for longitudinal movement within the pan relative to upper and lower jaw members 22, 24. The actuating members include a pusher block 180 which is disposed within module pan 172 for reciprocal, longitudinal movement within the pan. Pusher block 180 is attached to an actuator knob 182 by a lateral flange 184. When actuator module 170 is mounted within lower jaw 24, as shown in FIG. 3, flange 184 extends through an elongated guide slot 186 formed in a sidewall 64 of the lower jaw. Flange 184 positions knob 182 on the outside of jaw members 22, 24 to allow manual access of the knob. In FIG. 3, knob 182 is shown extending through a guide slot 186 in lower jaw sidewall 64b. However, a guide slot could also be formed in the opposite lower jaw sidewall 64a, in which case actuating knob 182 would extend out the opposite side of stapler 20. Flange 184 extends through and rides along guide slot 186 as knob 182 is manually moved along the outside of jaw members 22, 24.

Figure 22:
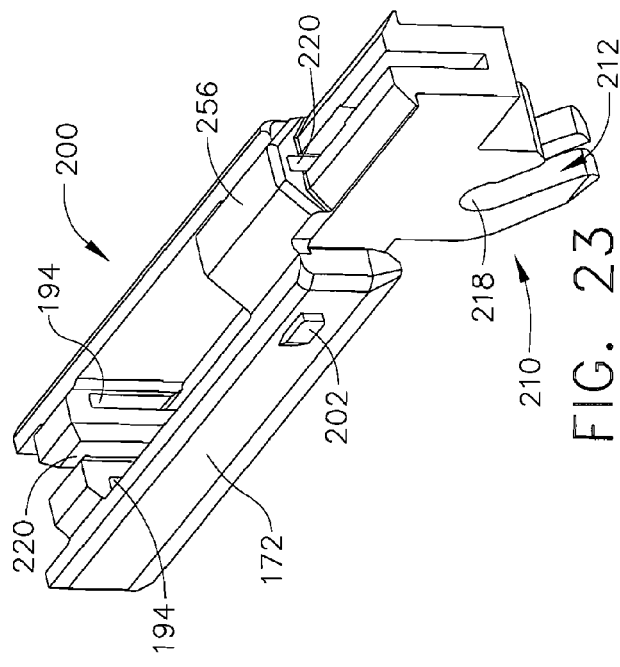
FIG. 22 is an isometric view of the actuating knob.
Figure 23:
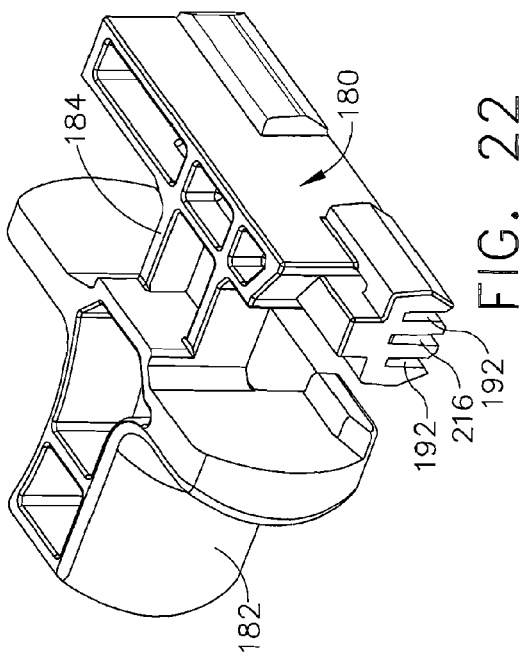
FIG. 23 is an isometric view of the guide block.
Figure 24:
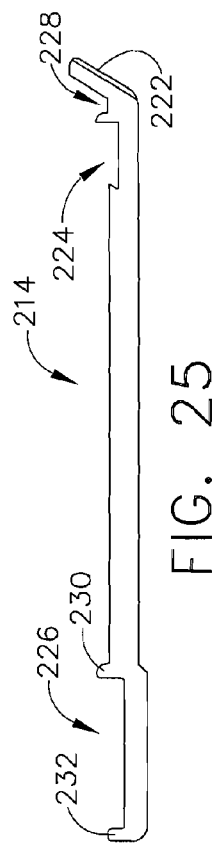
FIG. 24 is an isometric view of a pusher bar.

Returning now to FIG. 21, actuator module 170 also includes a pair of longitudinally extending, parallel pusher bars 190. The proximal ends of pusher bars 190 are secured within laterally spaced pusher block slots 192 (shown in FIG. 22) to allow the pusher bars to move longitudinally with pusher block 180 through module pan 172. Pusher bars 190 extend distally from pusher block 180 and are slidably received in longitudinal slots 194 formed in a guide block 200, shown in FIG. 23. As shown in FIG. 18, guide block 200 is mounted at the distal end of module pan 172. The upper edges of module pan sidewalls 174 are bent inward over the side edges of guide block 200 to retain the guide block within the module pan. Additionally, tabs 202 extend from the sides of guide block 200 through openings 204 in module pan sidewalls 174 to secure the guide block within the pan. The distal end of guide block 200 extends beyond the end of module pan 172 and between rear flanges 104 of staple cartridge 90. Lateral slots 194 within guide block 200 align pusher bars 190 with the elongated staple driver slots 100 of staple cartridge 90. The distal ends of pusher bars 190 extend forward of guide slots 194 and are provided with a wedge-shaped tip 206, shown in FIG. 24, which defines an inclined cam surface for engaging the staple drivers within cartridge 90 as the pusher bars are moved distally through the cartridge. The longitudinal movement of the pusher bar tips 206 sequentially drives the staple drivers, through a camming action, to fire staplers from the cartridge.

Returning to FIG. 23, guide block 200 includes a depending center section 210 which extends downward through opening 76 in the lower jaw bottom wall 66. Center section 210 includes a distally angled, straight-sided slot 212 with a circular end 218. When stapler 20 is assembled, guide block slot 212 is longitudinally aligned with slot 82 in lower jaw sidewalls 64a, 64b to enable latch pin 122 to engage both lower jaw 24 and guide block 200 when latching member 30 is connected to the stapler. As latch pin 122 is inserted through slot 82 into slot end 88, the pin also passes through guide block slot 212 and lodges within circular end 218, locking the actuator module 170 and lower jaw 24 together.

Figure 25:
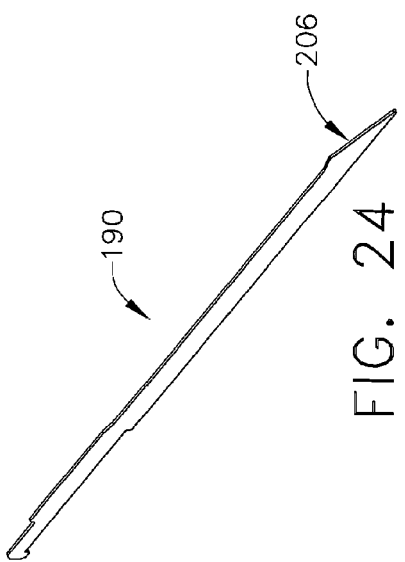
FIG. 25 is an isometric view of the knife support bar.

As shown in FIGS. 18 and 21, actuator module 170 further comprises a knife support bar 214 positioned between pusher bars 190. Knife support bar 214 and pusher bars 190 are preferably manufactured as sheet metal components. The proximal end of knife support bar 214 is secured within a center slot 216 of pusher block 180 (FIG. 22) to connect the knife support bar to the pusher block for movement by firing knob 182. Distal of pusher block 180, knife support bar 214 is slidably received in a center slot 220 formed in guide block 200 (shown in FIG. 23) to align the knife support bar with the elongated center slot 94 of the staple cartridge. As shown in FIG. 25, an inclined knife blade 222 having a beveled cutting edge is located at the front end of knife support bar 214. The beveled cutting edge of knife blade 222 is oriented at an angle relative to jaw members 22, 24, and is slidably received in central slot 220 of guide block 200. Proximal of knife blade 222, knife support bar 214 includes a cartridge locking notch 228 and a locking cut out section 224, which are part of a safety lockout mechanism described below. The proximal end of knife support bar 214 includes an offset section, indicated by reference number 226. Knife offset 226 is formed by cutting away a section of the knife support bar 214 near the proximal end, to produce two elevated points 230, 232 on the support bar.

Figure 27:
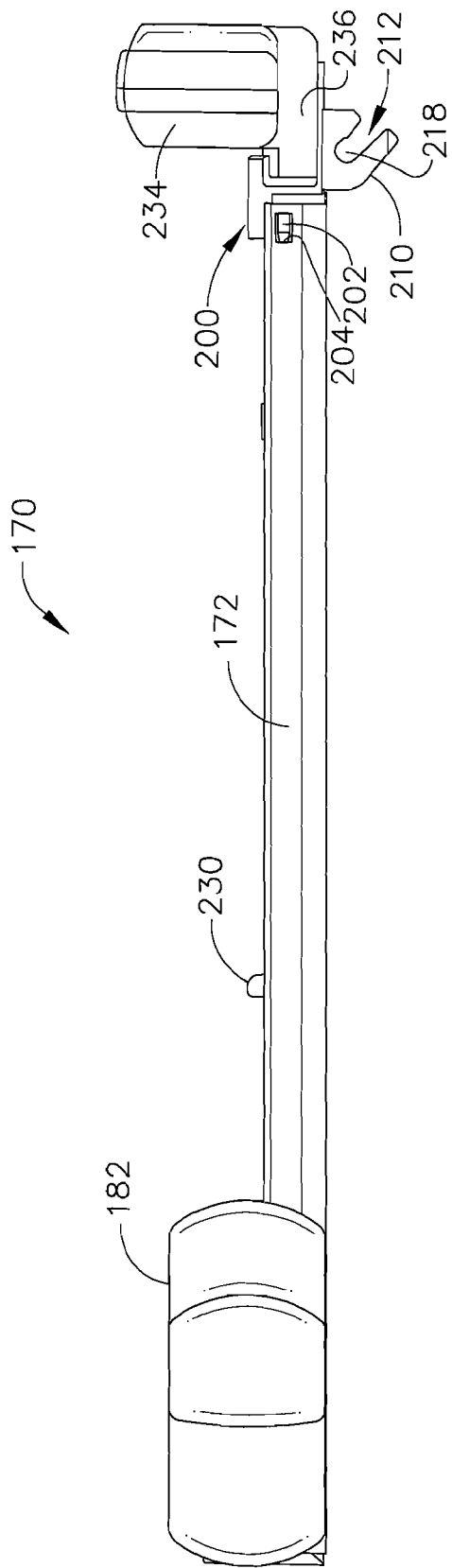
FIG. 27 is a front view of the actuating module.

As shown in FIGS. 26 and 27, a protector cap 234 covers the distal end of guide block 200. A center section 236 of cap 234 surrounds knife blade 222 and the wedged tips 206 of pusher bars 190. An inwardly directed lip 240 extends along the bottom edge of the cap. During assembly, downward pressure is applied to protector cap 234 to snap the distal end of the actuator module in place inside the lower jaw channel. As cap 234 is pressed downward, cap lip 240 snaps into indentations 74 on the outer surface of lower jaw 24.

A leaf spring 250, shown in FIG. 19, is integrated into module pan bottom wall 176 beneath guide block 200. Spring 250 provides a safety lockout feature by lifting knife support bar cut out 224 against guide block 200 after firing, to prevent re-firing of a used cartridge. A second spring 252 is integrated into module pan bottom wall 176 near the proximal end of the pan. This second spring 252 is a detent spring that interacts with a notch on pusher block 180 to prevent forward movement of actuator knob 182 during shipping, and to provide audible and tactile feedback when the actuator knob is returned to the proximal-most position in the module pan following firing. FIGS. 28 and 29 illustrate the operation of detent spring 252 in greater detail. In FIG. 28, spring 252 is shown engaging a notch 254 on pusher block 180 to prevent unintentional distal movement of the pusher block. FIG. 29 shows detent spring 252 disengaged from notch 254 by the application of an intentional, distally directed force on actuator knob 182. Pusher bars 190 and knife support bar 214 are advanced distally by applying sufficient force to actuator knob 182 to overcome the force of spring 252 against notch 254. After spring 252 is disengaged from notch 254, pusher block 180 can slide distally through module pan 172 to first advance pusher bars 190 and then advance knife support bar 214 from guide block 200 into staple cartridge 90.

In an initial firing position, shown in FIG. 28, a downwardly directed edge of pusher block 180 is in contact with knife support bar 214 at the proximal end point 232 of offset section 226. Actuating knob 182 is retracted to a fully proximal position within guide slot 186, thereby placing pusher bars 190 and knife blade 222 within slots 194 and 220 of guide block 200. When a distal pushing force is applied to actuating knob 182, spring 252 disengages from notch 254, enabling pusher block 180 to advance longitudinally within module pan 172. As pusher block 180 moves, the block advances pusher bars 190 distally, causing the inclined tips of the bars to advance into cartridge driver slots 100. During the initial movement of pusher block 180, the distal edge of the block moves through knife support bar offset 226, as shown in FIG. 29, thereby not making contact with the support bar itself. Knife support bar 214 thus remains stationary during the initial distal movement of the pusher bars 190 and block 180.

After pusher block 180 advances through knife offset section 226, the distal edge of the block contacts the distal end point 230 of knife support bar 214. This contact between pusher block 180 and knife support bar 214 causes the knife support bar to begin advancing distally, along with the pusher block and pusher bars 190, as knob 182 is advanced. As knife support bar 214 moves distally, knife blade 222 is guided by central slot 220 and rear cartridge extension 116 into central longitudinal slot 94 of staple cartridge 90 and central longitudinal slot 46 of anvil 44. As knife blade 222 advances through cartridge extension 116, the blade deflects lock out pin 106 out of the path of the advancing support bar. Knife blade 222 and pusher bar tips 206 advance simultaneously through staple cartridge 90 driving staples through openings 96 and cutting tissue. Knife blade 222 is advanced into staple cartridge 90 slightly behind pusher bars 190 so that staples are formed into the tissue gripped between the anvil and cartridge prior to the knife blade advancing and cutting the tissue between the staple rows.

After the knife and pusher bars have been fully advanced by knob 182 (or advanced to the desired forward position), pusher block 180 is retracted within module pan 172 by drawing the actuating knob back proximally through jaw guide slot 186. Initially, as pusher block 180 is drawn proximally, pusher bars 190 are drawn proximally while knife support bar 214 remains in a distal, stationary position due to the offset section 226 in the support bar. As the distal pusher block edge retracts into contact with proximal knife bar offset point 232, the knife support bar 214 begins to retract proximally with the pusher block and bars. As knife support bar 214 retracts within guide block 200, the support bar is lifted up by leaf spring 250 into contact with the guide block, until the knife locking cut out 224 catches a center post 256 (FIG. 23) of the guide block. Once knife cut out 224 engages guide block post 256, knife support bar 214 is prevented from further movement in conjunction with pusher block 180. Preferably, knife support bar 214 engages locking cut out section 224 as pusher block 180 and pusher bars 190 are reaching the fully proximal position.

After actuator knob 182 is fully retracted, as shown in FIG. 28, latching member 30 is pivoted relative to jaw members 22, 24 to separate the upper and lower jaws, as described above. With the jaw members separated, staple cartridge 90 can be removed and replaced with a new cartridge. The used cartridge can be removed by pulling up on cartridge wings 114 to dislodge cartridge legs 110 from lower jaw opening 76. As the proximal end of the staple cartridge is lifted out of lower jaw opening 76, cartridge leg notches 112 (FIG. 7) are drawn out of engagement with latch pin 122. After the proximal end of staple cartridge 90 is dislodged, the cartridge can be slid distally out of cartridge channel 70 and discarded.

A new staple cartridge 90 can be loaded into lower jaw 24 by pushing the flanged, distal end of the cartridge against the distal end of the lower jaw cartridge channel 70, and pushing down on wings 114 to lower legs 110 through jaw opening 76. Cartridge legs 110 are pushed through lower jaw opening 76 until leg notches 112 snap onto latch pin 122. As the proximal end of staple cartridge 90 is pushed down, lockout pin 106 on the cartridge depresses knife support bar 214 at locking notch 228 against the counter force of leaf spring 250. The force of lockout pin 106 pushes knife support bar cutout 224 down and out of contact with guide block center post 256. As knife support bar 214 is pushed down, the support bar is realigned with guide block center slot 220 to enable the support bar to pass distally through the slot and into the new cartridge. The safety lockout feature is thus reset during loading of a new staple cartridge. With a new cartridge loaded, the stapler can be reassembled by placing upper jaw 22 over lower jaw 24 and reinserting upper jaw pins 54 into lower jaw alignment slots 56. Latching hook members 140 are pivoted back over the opening of slots 56 until pins 54 are lodged within notches 142. With pins 54 locked within hook member notches 142, and latching member 30 pivoted into position about lower jaw 24, the stapler is closed and ready to fire staples from the new cartridge.

The reusable upper and lower jaw and latching member components described above are provided to a user in a non-sterile package. Prior to assembly of stapler 20, the components are cleaned with pH neutral enzymatic cleaners, and then steam autoclaved to sterilize the components. This conditioning procedure is also followed prior to each subsequent reuse of the components. Actuator module 170, due to it multiple movable components, is designed for single patient use to eliminate the complexity of cleaning the module. The actuator module is provided to the user in a sterile disposable package which is opened in the sterile field. Staple cartridge 90 is also delivered as a sterile disposable package that is opened in the sterile field.

To assemble stapler 20, actuator module 170 is removed from its packaging and inserted proximal end first into the proximal channel of lower jaw member 24. Actuator module 170 snaps into place when proximal detent bumps 178 engage lower jaw retention features 86. The distal end of the actuator module is then rotated down into the channel shaped frame of lower jaw 24. With actuator module 170 within the lower jaw channel, protector cap 234 is pushed down to snap cap lips 240 into indentations 74 on the lower jaw sidewalls 64a, 64b. Pushing down on protector cap 234 pushes guide block center section 212 through lower jaw opening 76, aligning guide block slot 212 with lower jaw slot 82, and locking the actuator module in place within the lower jaw member 24. With actuator module 170 loaded into lower jaw member 24, latching member 30 is attached to the lower jaw by inserting latch pin 122 into slots 82 and 212, as described above. Latching member 30 is rotated relative to lower jaw member 24 to the partial locked-in position shown in FIG. 14. In this position, latching member 30 is attached to lower jaw member 24, but upper jaw 22 is separable from the lower jaw. Protector cap 234 is removed from actuator module 170 by moving the cap in the distal direction, as indicated by the arrow on the cap shown in the Figures.

A new staple cartridge 90 is next inserted into lower jaw cartridge channel 70 in the manner described above. After a staple cartridge is loaded, upper jaw member 22 is placed over lower jaw member 24, with pins 54 inserted into alignment slots 56. Latching member 30 is pivoted relative to the upper and lower jaw members 22, 24 to place the stapler into the pre-close position (shown in FIG. 15), in which the hook member cam surfaces 144 extend over the openings to alignment slots 56 to prevent pins 54 from disengaging from the slots. The tissue to be transected is placed between the anvil 44 and staple cartridge 90 and adjusted to the desired position. Tissue stops 52 prevent the tissue from being positioned too far back into the stapler. With the tissue properly situated, the stapler is closed in preparation for firing by rotating latching member 30 into contact with lower jaw 24 to place hook member 140 over slots 56, and lock pins 54 inside hook member notches 142. In this state, the tissue is clamped within the device. If additional tissue adjustment is required, the stapler can be returned to the pre-close state, as shown in FIG. 16, in which the distal ends of the upper and lower jaw members can move slightly relative to each other to accommodate tissue repositioning. With the tissue properly clamped between the jaw members, and latching member 30 pivoted to the closed, operative position, the stapler can be fired by pushing actuator knob 182 forward through guide slot 186 until the knob stops. As the knob advances, the clamped tissue is stapled and cut. After actuator knob 182 reaches its distal stop, the knob is drawn back proximally through guide slot 186. At the proximal end of the knob path, the interaction of detent spring 252 and push block notch 254 provides tactile and audible feedback that the knob is fully retracted, signaling that the actuating components have been withdrawn from staple cartridge 90 back into module pan 172.

If additional stapling and cutting is desired to complete the procedure, latching member 30 is pivoted back to the partially locked-in state so that upper jaw 22 can be removed, and the used staple cartridge discarded and replaced with a new staple cartridge. After the new cartridge is in place, latching member 30 can be pivoted back through the pre-close and closed states to enable tissue to again be positioned, clamped and stapled using the new cartridge. Once all the required tissue is transected, latching member 30 is removed by rotating the member back to the open state (shown in FIG. 13), and sliding latch pin 122 out of slots 82 and 212. The actuating module 170 and staple cartridge 90 can then be removed from lower jaw member 24 and discarded. The remaining components (upper jaw, lower jaw, and latching member) can be cleaned and sterilized as separate components in preparation for reuse.

In the present invention, actuator module 170 is a separate component from staple cartridge 90, enabling spent staple cartridges to be replaced during a single patient procedure without replacing the actuator module. Accordingly, the actuator module may be used multiple times in the same patient with different staple cartridges. Using the single piece module pan 172 as a supporting structure for the actuator module components enables the actuator module to be easily assembled into and disassembled from the lower jaw channel. The reusable stapler components have a simple, single piece design to facilitate repeated reconditioning and reuse of the parts. The detachable design of the latching member facilitates easy disassembly and reassembly of the reusable components of the stapler. Further, once the stapler is assembled, the retaining and locking features of the latching and lower jaw members prevent accidental disassembly during a procedure.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method for performing a surgical stapling procedure, said method comprising:
   a. providing a surgical stapler comprising a body having a distal end, a proximal end and a longitudinal axis therebetween, said proximal end comprising a handle and a distal end comprising a first staple cartridge and an opposing anvil, said first staple cartridge containing a plurality of surgical staples, said surgical stapler further including a first actuator module for deploying staples, said first actuator including a longitudinally movable member for sequentially ejecting staples towards said anvil;
   b. operating said first actuator module so as to eject said plurality of staples from said first staple cartridge;
   c. removing said first staple cartridge from said body and discarding said first staple cartridge, inserting a second staple cartridge into said body, said second staple cartridge containing a plurality of surgical staples;
   d. operating said first actuator module so as to eject said plurality of staples from said second staple cartridge;
   e. removing said first actuator module from said body and discarding said first actuator module;
   f. sterilizing said body, inserting a second actuator module and a staple cartridge into said body, and operating said actuator module so as to eject said plurality of staples.

* * * * *